United States Patent
Kozak

(10) Patent No.: US 8,394,036 B2
(45) Date of Patent: Mar. 12, 2013

(54) METHOD AND APPARATUS FOR DETERMINING THE ANGULAR POSITION OF AN ACETABULUM IN A PELVIC BONE

(75) Inventor: Josef Kozak, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1168 days.

(21) Appl. No.: 12/284,619

(22) Filed: Sep. 22, 2008

(65) Prior Publication Data

US 2009/0105714 A1    Apr. 23, 2009

(30) Foreign Application Priority Data

Oct. 17, 2007  (DE) .......................... 10 2007 049 668

(51) Int. Cl.
*A61B 5/103* (2006.01)
(52) U.S. Cl. ........................ 600/587; 600/407; 606/102
(58) Field of Classification Search ................. 600/426, 600/407; 606/102
See application file for complete search history.

(56) References Cited

U.S. PATENT DOCUMENTS

| | | | |
|---|---|---|---|
| 5,966,827 A | 10/1999 | Horvath et al. | |
| 6,621,247 B1 | 9/2003 | Bulling et al. | |
| 6,669,653 B2 | 12/2003 | Paltieli | |
| 2002/0077540 A1 | 6/2002 | Kienzle, III | |
| 2004/0254584 A1* | 12/2004 | Sarin et al. ..................... | 606/102 |
| 2004/0254586 A1 | 12/2004 | Sarin et al. | |
| 2005/0148855 A1* | 7/2005 | Kienzle, III ................... | 600/407 |
| 2005/0203540 A1 | 9/2005 | Broyles | |
| 2006/0004284 A1 | 1/2006 | Grunschlager et al. | |
| 2006/0036397 A1 | 2/2006 | Dick | |
| 2006/0084889 A1 | 4/2006 | Drumm et al. | |
| 2006/0095047 A1 | 5/2006 | de la Barrera | |
| 2008/0056433 A1 | 3/2008 | Steinle et al. | |
| 2008/0132783 A1* | 6/2008 | Revie et al. ..................... | 600/426 |
| 2008/0269757 A1 | 10/2008 | McMinn | |
| 2009/0171370 A1 | 7/2009 | Yoon et al. | |
| 2009/0306679 A1 | 12/2009 | Murphy | |
| 2010/0030231 A1 | 2/2010 | Revie et al. | |

FOREIGN PATENT DOCUMENTS

| | | |
|---|---|---|
| DE | 103 11 454 | 10/2004 |
| DE | 103 49 938 | 6/2005 |
| DE | 20 2005 009 777 | 1/2006 |
| DE | 10 2005 003 317 | 7/2006 |
| DE | 11 2005 002 453 | 8/2007 |
| EP | 0 944 354 | 9/1999 |
| EP | 1579803 | 9/2005 |

(Continued)

OTHER PUBLICATIONS

Nagamune, et al., "Estimation System of Affection Due to Pointing Error in Navigation System of Total Hip Arthroplasty", IEEE Xplore Digital Library, Dec. 9, 2008, 6 pages.

*Primary Examiner* — Max Hindenburg
*Assistant Examiner* — Renee Danega
(74) *Attorney, Agent, or Firm* — Lipsitz & McAllister, LLC

(57) ABSTRACT

In a method for determining the angle of anteversion and/or the angle of inclination of an acetabulum in a pelvic bone, in order to achieve a simplification, a method is proposed, wherein prominent points on the pelvic bone are non-invasively determined, these prominent points are joined by an individual plane, and this individual plane is respectively rotated through predetermined, specific angular magnitudes for the angle of inclination and the angle of anteversion, respectively, and the angle between the rotated individual plane and a main plane of the pelvic bone is determined in order to determine the angle of inclination and the angle of anteversion.

12 Claims, 6 Drawing Sheets

FOREIGN PATENT DOCUMENTS

| | | |
|---|---|---|
| EP | 1 611 863 | 1/2006 |
| WO | 2004/030556 | 4/2004 |
| WO | 2005/084541 | 9/2005 |
| WO | WO 2005/084541 | 9/2005 |

\* cited by examiner

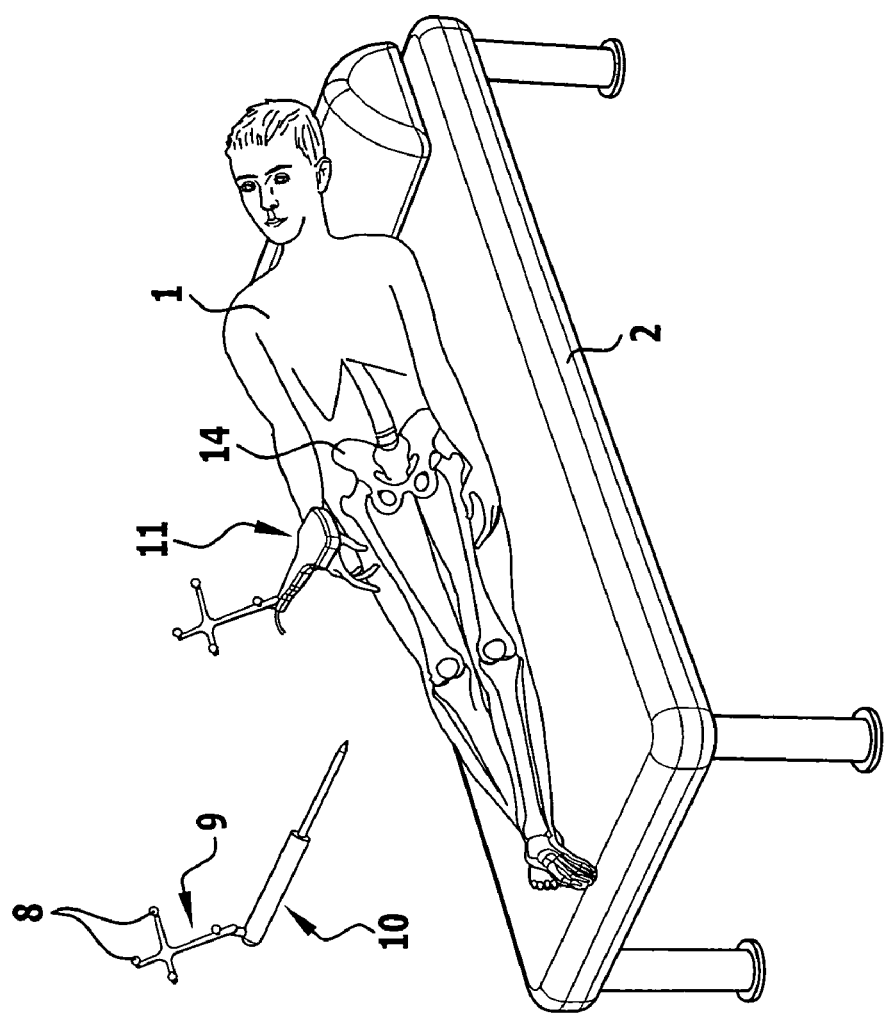
FIG.1
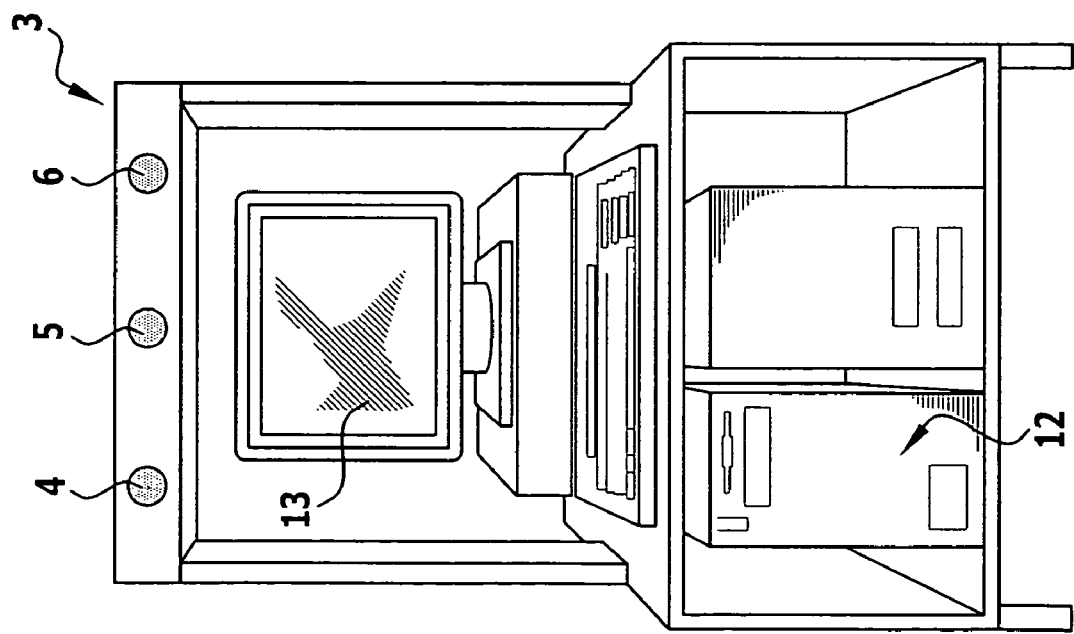

METHOD AND APPARATUS FOR DETERMINING THE ANGULAR POSITION OF AN ACETABULUM IN A PELVIC BONE

The present disclosure relates to the subject matter disclosed in German application number 10 2007 049 668.2 of Oct. 17, 2007, which is incorporated herein by reference in its entirety and for all purposes.

BACKGROUND OF THE INVENTION

The invention relates to a method for determining the angle of anteversion and/or the angle of inclination of an acetabulum in a pelvic bone.

When implanting an acetabulum, which generally has as an approximately hemispherical shape, the position of the acetabulum and its angular position relative to the pelvic bone must be precisely determined before the implantation. The position can be determined relatively easily by the center point of rotation of the hip joint being determined prior to the implantation, for example, by pivoting the femur relative to the pelvic bone. This center point then corresponds to the spherical center point of the hemispherical acetabulum.

The determination of the angular position of the acetabulum proves more difficult. The acetabulum has a bottom rim which defines a plane delimiting the hemispherical acetabulum at the bottom end, and there extends perpendicularly to this plane a central axis of the hemispherical acetabulum, which passes through the center point of the acetabulum. This central axis of the acetabulum is generally arranged in space such that it includes different angles with the main planes of the pelvic bone. Main planes of the pelvic bone are to be understood as the transverse plane, i.e., a plane extending horizontally in an upright pelvis, the sagittal plane, i.e., a plane running from front to back and extending perpendicularly to the transverse plane in an upright pelvis, and the frontal plane which extends perpendicularly to the two aforementioned planes.

To describe the position of the central axis relative to these main planes, it is standard practice to indicate the angle of anteversion and the angle of inclination. The angle of anteversion describes the angle which an anteversion plane containing the central axis and extending perpendicularly to the transverse plane includes with a frontal plane. The angle of inclination describes the angle which an inclination plane extending perpendicularly to the central axis of the acetabulum and extending perpendicularly to a frontal plane assumes relative to a sagittal plane.

In practice, the angle of anteversion and the angle of inclination are determined by complicated preliminary examinations carried out on the patient, for example, by X-rays taken in various planes or by ultrasonic examinations, which involve a great deal of expenditure, and, in particular, in the case of X-ray examinations, expose the patient to a high dose of radiation.

SUMMARY OF THE INVENTION

The object of the invention is to provide a method for determining these angular magnitudes, with which the angle of anteversion and/or the angle of inclination can be determined, where necessary, during the operation, in a simple way.

This object is accomplished, in accordance with the invention, for determination of the angle of anteversion, by a method wherein the position of the spina iliaca anterior superior (anterior superior iliac spine) at one side of the pelvic bone is non-invasively determined, and the position of the spina iliaca posterior superior (posterior superior iliac spine) at the same side is non-invasively determined, a plane extending perpendicularly to a transverse plane of the pelvic bone is made to pass through these points, this plane is rotated about an axis of rotation extending perpendicularly to the transverse plane through a predetermined angular magnitude of between 35.6° and 40.4°, and the angle between the rotated plane and a frontal plane is determined as angle of anteversion.

The predetermined angular magnitude is preferably 38°.

The object is accomplished, in accordance with the invention, for determination of the angle of inclination by a method wherein the position of the spina iliaca anterior superior (anterior superior iliac spine) at one side of the pelvic bone is non-invasively determined, and, in addition, the position of the symphysis pubis (pubic symphysis) is non-invasively determined, a plane extending perpendicularly to a frontal plane of the pelvic bone is made to pass through these points, this plane is rotated about an axis of rotation extending perpendicularly to the frontal plane through a predetermined angular magnitude of between 14.1° and 17.9°, and the angle between the rotated plane and a sagittal plane is determined as angle of inclination.

The predetermined angular magnitude is preferably 16°.

Accordingly, in the described method it is sufficient to non-invasively determine a few prominent points of the pelvic bone, which can be done, for example, by palpating prominent points of the pelvic bone through the skin or by an ultrasonic examination, and from these points and data relating to the main planes of the pelvic bone and by using the predetermined angular magnitude, both the angle of anteversion and the angle of inclination can be calculated. Values for the angle of anteversion and the angle of inclination are obtained, which depend upon the respective geometry of the pelvic bone, i.e., which can be individually determined for each individual pelvic bone. This does not require complicated X-ray examinations.

The object set forth hereinabove is also accomplished by an apparatus which operates in accordance with the methods described hereinabove.

The following description of preferred embodiments of the invention serves in conjunction with the drawings for a more detailed explanation.

BRIEF DESCRIPTION OF THE DRAWINGS

FIG. 1 shows a schematic representation of a patient lying on an operating table and a navigation system for detecting the position of navigated position sensors;

DETAILED DESCRIPTION OF THE INVENTION

Figure 2:
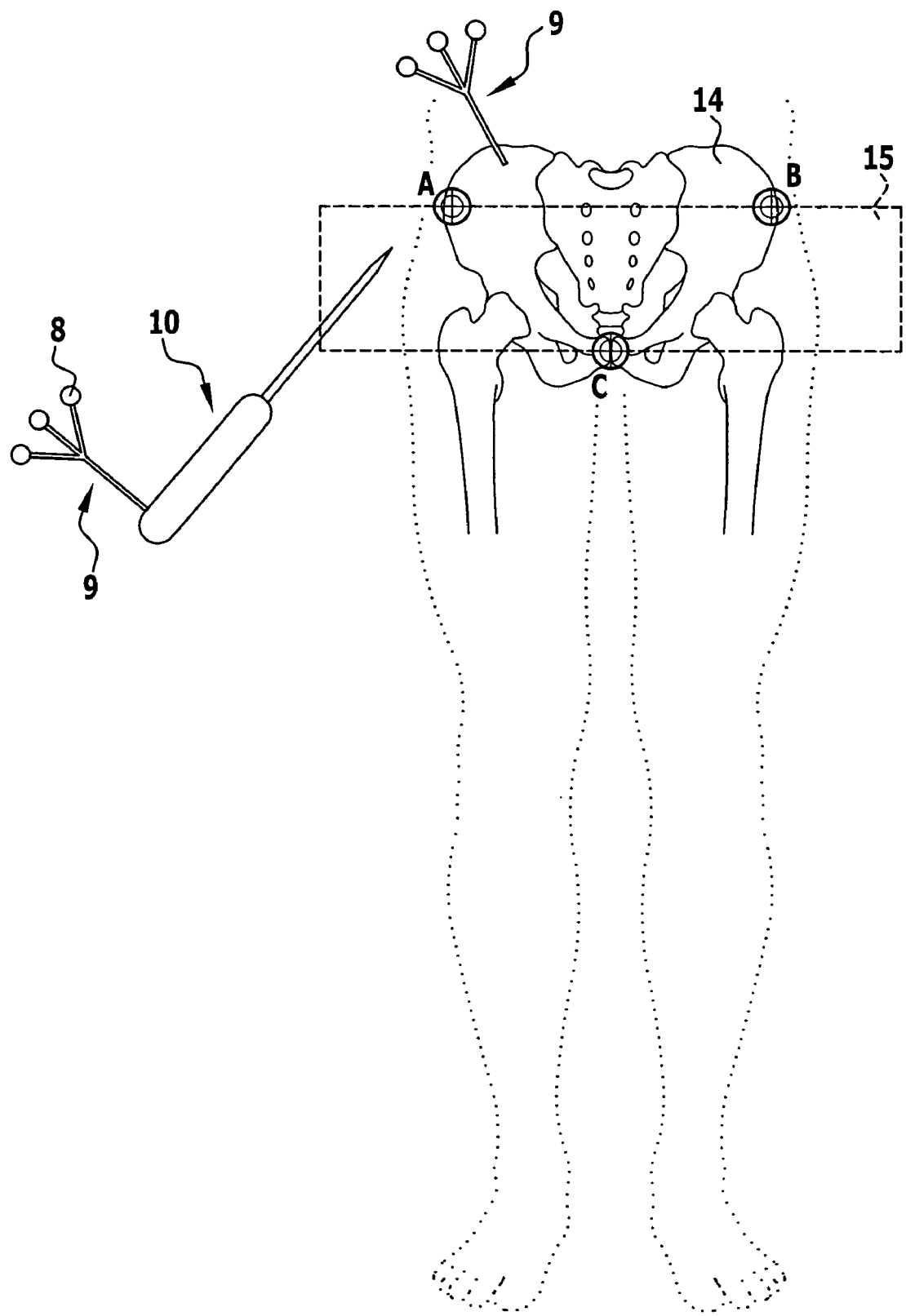
FIG. 2 shows a schematic front view of a patient while determining a frontal plane of the pelvic bone.

There is shown in FIG. 1 a patient 1 lying on an operating table 2. Operations may be carried out on the patient in this position. Located beside the operating table 2 is a navigation system 3 with a number of radiation emitters 4, 5, 6, which at the same time are also configured as radiation receivers. The emitted radiation may be infrared radiation. This radiation is reflected by reflective surfaces 8, which may be spheres arranged as markers 9 on various instruments 10, for example, a palpation instrument 10 and an ultrasonic sensor 11.

The navigation system is therefore able to detect in a manner known per se the position of the instruments in space, i.e., their exact position and their orientation.

A data processor 12 with a display device 13, in the form of a monitor in the embodiment shown, is also associated with the navigation system 3.

To enable the position of a patient's pelvic bone 14 to be described, it is known to use three prominent points of the pelvic bone, which define a so-called pelvic inlet plane. This is a special frontal plane which is identified by special prominent points lying in this frontal plane. These prominent points are the following points:

A) spina iliaca anterior superior left
(left anterior superior iliac spine)
B) spina iliaca anterior superior right
(right anterior superior iliac spine)
C) symphysis pubis
(pubic symphysis).

These three points may be palpated percutaneously, for example, by hand or with the aid of the navigated palpation instrument 10. It is also possible to detect these points with the aid of the navigated ultrasonic sensor. In any case, it is in this way possible to locate the position of the three points A), B) and C) in space, and the navigation system can forward a set of data corresponding to the position of points A), B) and C) to the data processor 12.

The position of the pelvic bone in space is defined by the determination of these points. This plane serves as reference plane for all further determinations of location and orientation.

Figure 3:
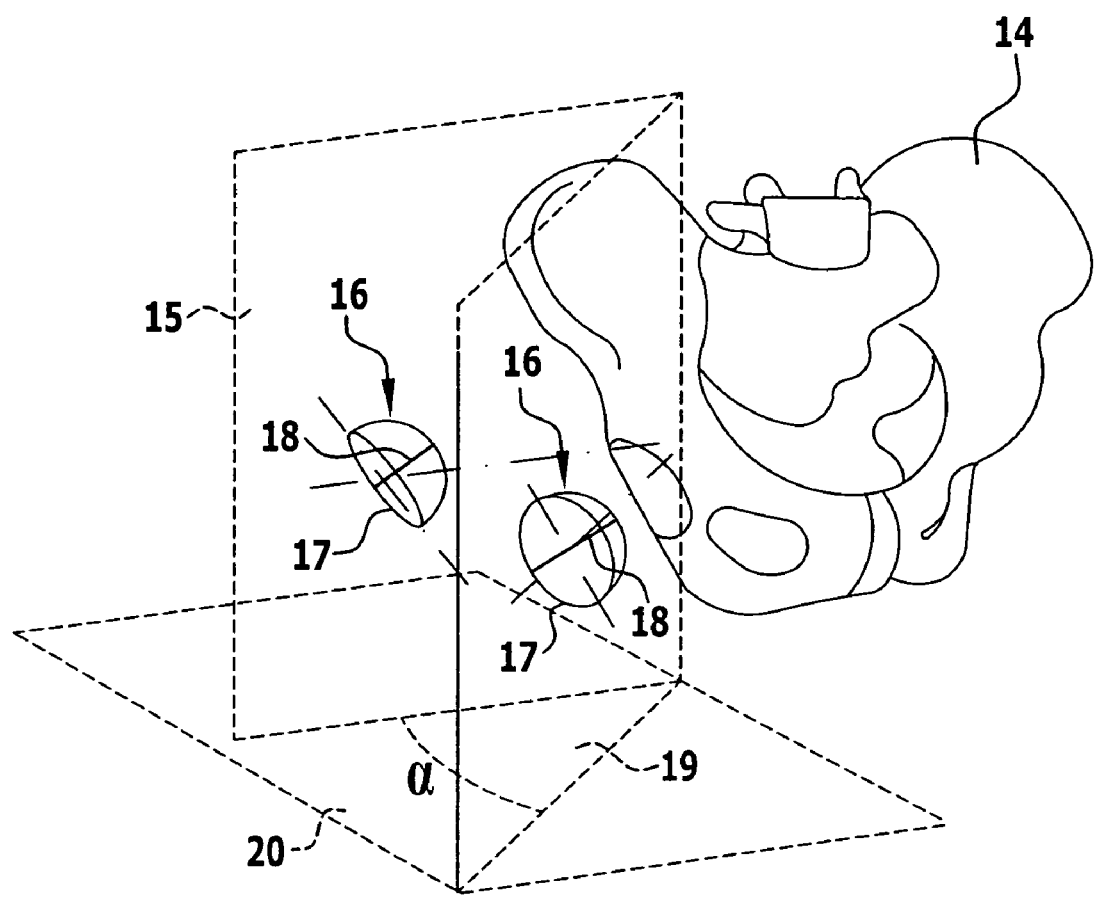
FIG. 3 shows a schematic view of a pelvic bone, a frontal plane, a transverse plane and an anteversion plane.

FIG. 3 shows a pelvic bone 14 and, in addition, a frontal plane 15. An acetabulum 16 is drawn schematically therein, more particularly, in such a way that a bottom terminating plane of the acetabulum 16 spanned by the bottom rim 17 extends perpendicularly to the frontal plane 15. Therefore, a central axis 18 of the acetabulum, which extends perpendicularly to this bottom terminating plane of the acetabulum 16 and passes through the center point of the hemispherical acetabulum 16, lies in the frontal plane 15 in the illustration in FIG. 3.

Such an arrangement of the acetabulum would correspond to an angle of anteversion of O° which is, however, not realistic.

In reality, the central axis 18 of the acetabulum 16 lies in an anteversion plane 19 which, like the frontal plane 15, extends perpendicularly to a transverse plane 20 and is rotated in relation to the frontal plane 15 about an axis of rotation extending perpendicularly to the transverse plane 20. The angle $\alpha$ included between the anteversion plane 19 and the frontal plane 15 is referred to as angle of anteversion.

Figure 4:
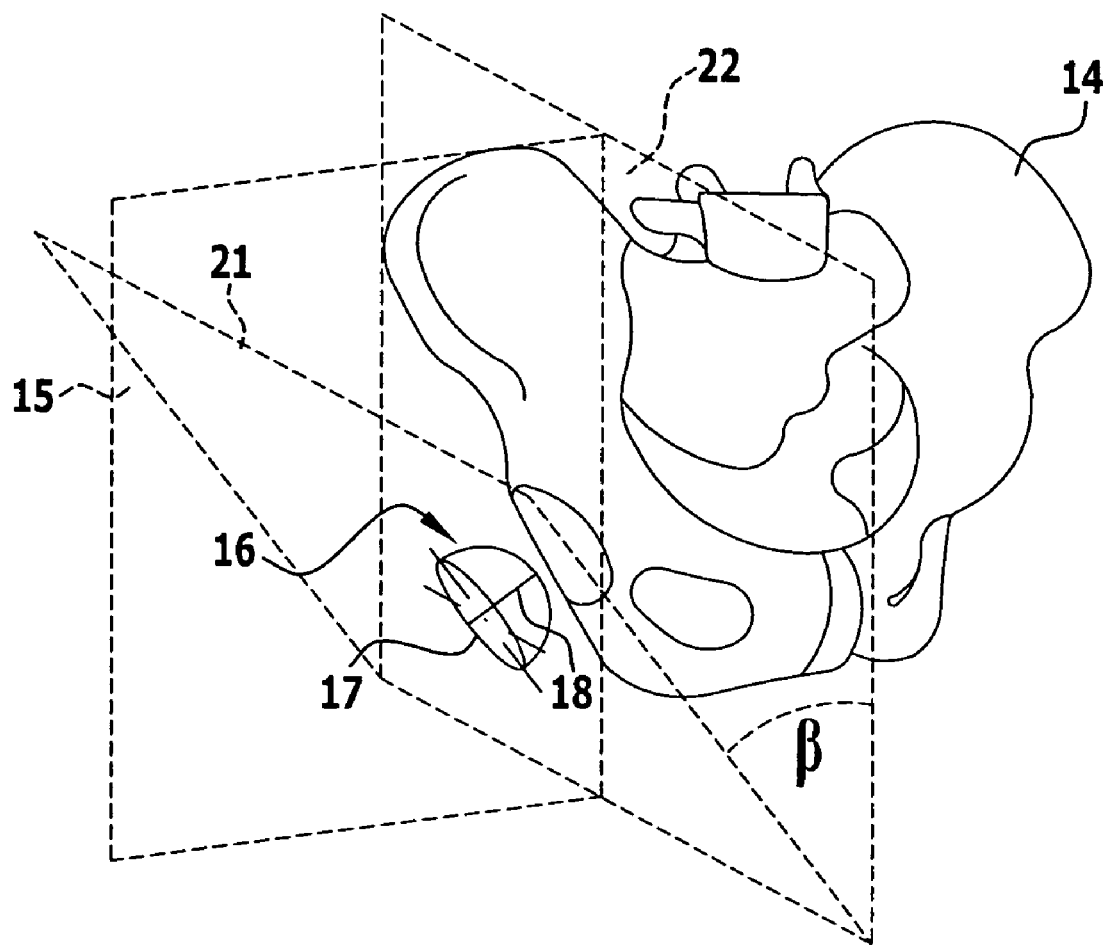
FIG. 4 shows a view similar to FIG. 3 with a frontal plane, a sagittal plane and an inclination plane.

In a similar way, a pelvic bone 14 is shown in FIG. 4 together with a frontal plane 15 and a sagittal plane 22 and, in addition, with an inclination plane 21, which coincides with the bottom terminating plane spanned by the bottom rim 17 of the acetabulum 16. The inclination plane 21 corresponds to the actual position in which the acetabulum 16 is incorporated into the pelvic bone 14, as does the anteversion plane 19 correspond to the actual position in which it is incorporated therein.

The angle $\beta$ between the inclination plane 21 and the sagittal plane 22 is referred to as angle of inclination.

Figure 5:
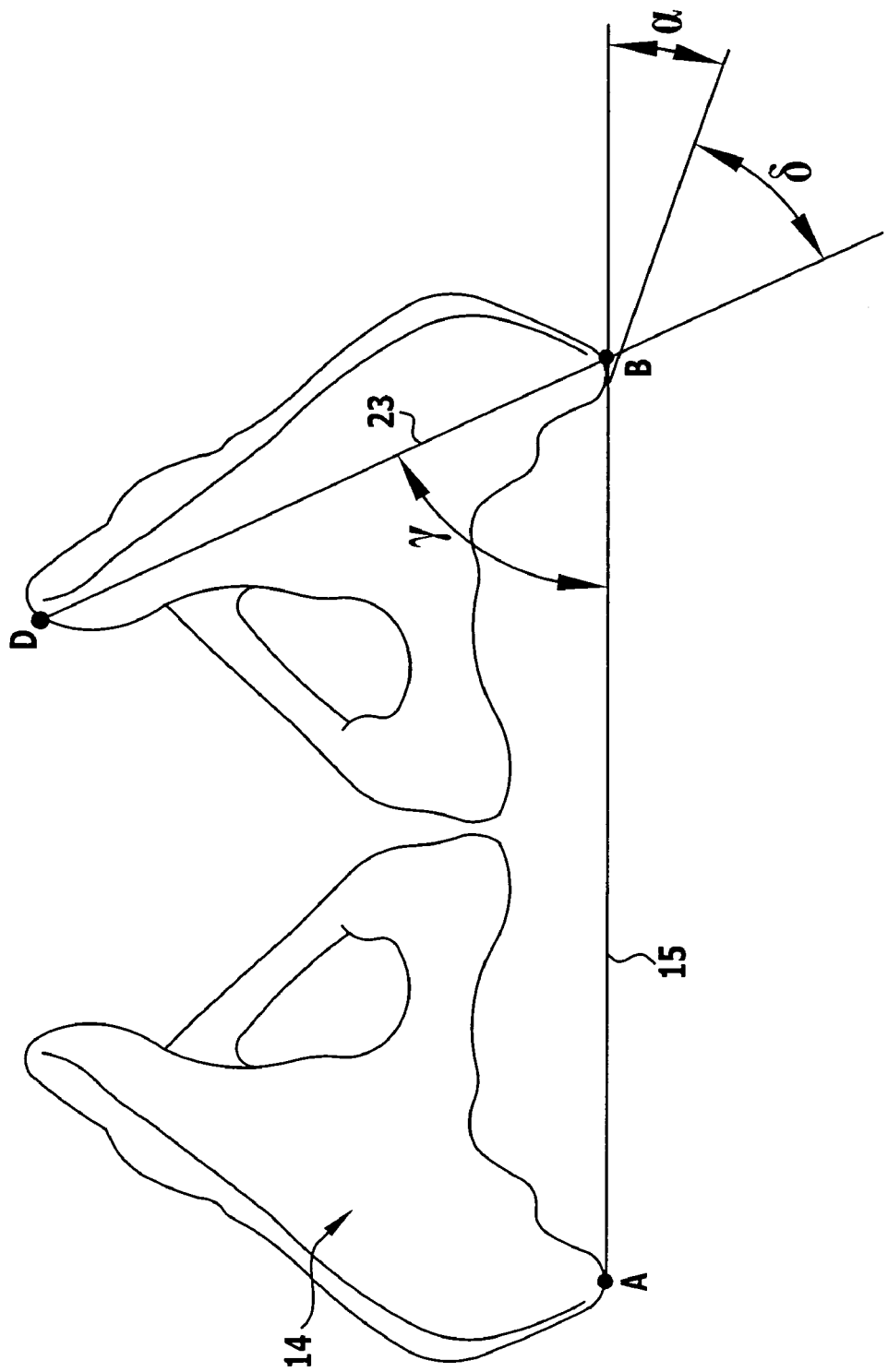
FIG. 5 shows a schematic plan view of a transverse plane of a pelvic bone with an individual plane passing through prominent points of the pelvic bone.

To determine the angle of anteversion, a further prominent point of the pelvic bone 14, as will be apparent from the schematic representation in FIG. 5, is additionally determined non-invasively in the manner described hereinabove, namely point D) spina iliaca posterior superior (posterior superior iliac spine). An individual plane 23, which extends perpendicularly to a transverse plane, is made to pass through this additionally determined point D) and through the spina iliaca anterior superior (anterior superior iliac spine) on the same side of the pelvic bone 14. This plane includes an individual angle $\gamma$ with the frontal plane 15.

In a further step, the individual plane 23 is rotated about an axis of rotation extending perpendicularly to the transverse plane through a predetermined angle $\delta$, which for determination of the angle of anteversion ranges from between 35.6° and 40.4° and is preferably 38°. After the rotation, the rotated plane includes an angle with the frontal plane 15, and this angle is the angle of anteversion $\alpha$. Accordingly, after the rotation, the rotated plane forms the anteversion plane 19 or coincides with it.

Figure 6:
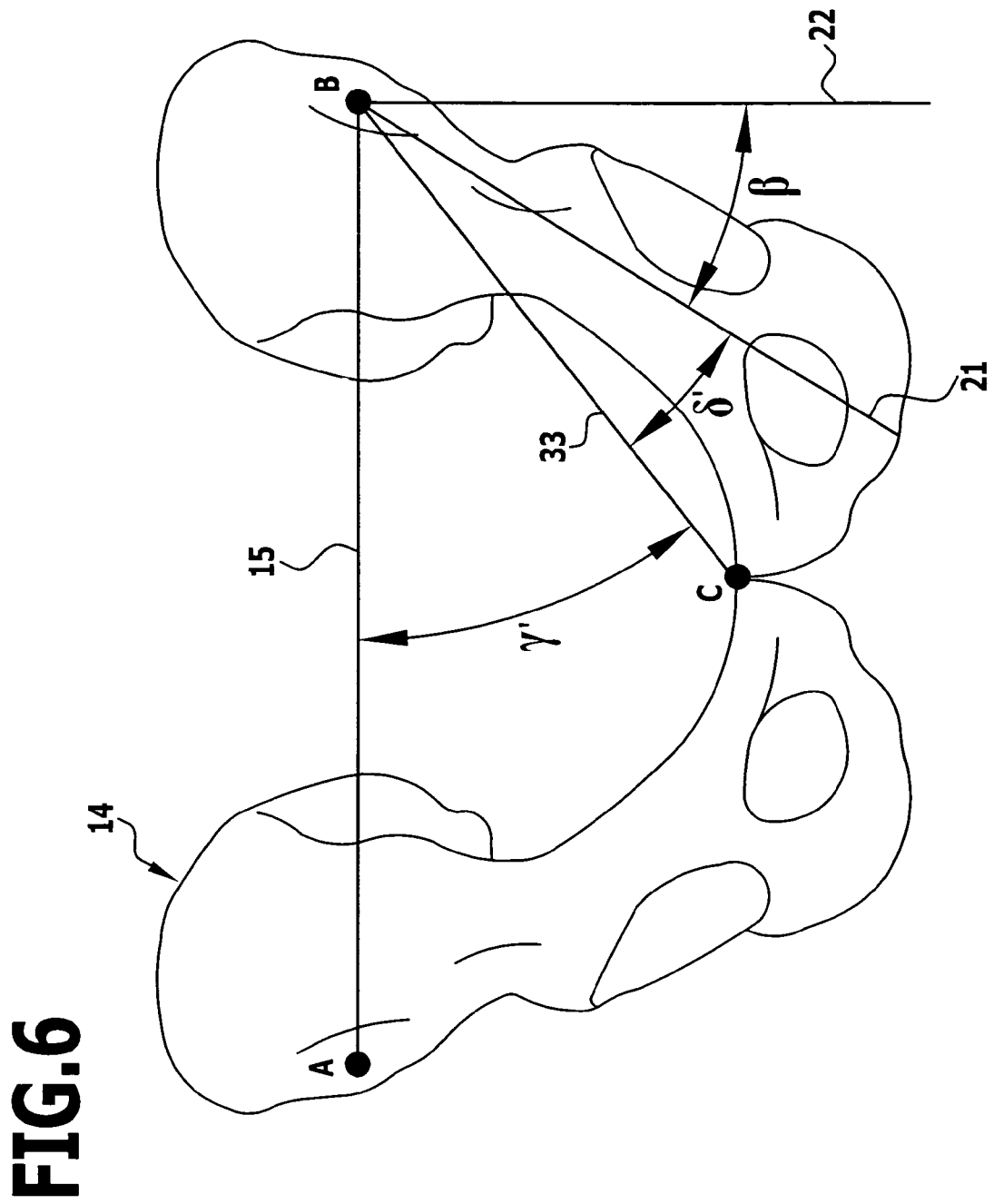
FIG. 6 shows a plan view of a frontal plane of the pelvic bone with an individual plane passing through prominent points of the pelvic bone.

In a similar way, the angle of inclination is determined in the manner shown schematically in FIG. 6. An individual plane 33, which extends perpendicularly to a frontal plane 15 and includes with it an individual angle $\gamma'$, is made to pass through points B) and C), i.e., through the spina iliaca anterior superior (anterior superior iliac spine) on one side of the pelvic bone and through the symphysis pubis (pubic symphysis). This individual plane 33 is then rotated about an axis of rotation extending perpendicularly to the frontal plane through a predetermined angle $\delta'$, which for determination of the angle of inclination ranges between 14.1° and 17.9° and is preferably 16°. After the rotation, the individual plane 33 coincides with the plane of inclination 21, which includes an angle of inclination $\beta$ with a sagittal plane 22.

Accordingly, merely by determining the position of the prominent points of the spina iliaca anterior superior (anterior superior iliac spine) and the spina iliaca posterior superior (posterior superior iliac spine) and of the symphysis pubis (pubic symphysis), it is possible to determine values for the angle of anteversion and the angle of inclination, which are individually dependent upon the shape of the pelvic bone 14, without complicated X-ray examinations or the like having to be carried out.

The method steps described hereinabove can be readily performed by the data processor 12 on the basis of the position data made available by the navigation system 3, so that the values of the angle of inclination and the angle of anteversion can be displayed to the operating surgeon immediately after determination of the position of the described prominent points.

Surprisingly, it has been found that the predetermined magnitudes of the angles through which the planes connecting the prominent points, i.e., the individual planes, must be rotated, in order to transfer them to the inclination plane and the anteversion plane, respectively, may be utilized independently of the individual dimensions of the pelvic bones in different patients, and that results are obtained for the values of the angle of inclination and the angle of anteversion that readily correspond to those achieved by much more complicated X-ray examinations.

The invention claimed is:
1. A method for determining an angle of anteversion of an acetabulum in a pelvic bone, comprising:
non-invasively determining a position of an anterior superior iliac spine at one side of the pelvic bone, non-invasively determining a position of a posterior superior iliac spine at the one side of the pelvic bone, passing a plane extending perpendicularly to a transverse plane of the pelvic bone through points defined by position data of the anterior superior iliac spine and of the posterior superior iliac spine, rotating the plane about an axis of rotation extending perpendicularly to the transverse plane through a predetermined angular magnitude of 38°, and determining an angle between the rotated plane and a frontal plane as an angle of anteversion.

2. A method for determining an angle of inclination of an acetabulum in a pelvic bone, comprising:

non-invasively determining a position of an anterior superior iliac spine at one side of the pelvic bone, non-invasively determining a position of pubic symphysis, passing a plane extending perpendicularly to a frontal plane of the pelvic bone through points defined by position data of the anterior superior iliac spine and of the pubic symphysis, rotating the plane about an axis of rotation extending perpendicularly to the frontal plane through a predetermined angular magnitude of 16°, and determining an angle between the rotated plane and a sagittal plane as an angle of inclination.

3. The method in accordance with claim 1, wherein the position of the anterior superior iliac spine and of the posterior superior iliac spine is determined by percutaneous palpation.

4. The method in accordance with claim 2, wherein the position of the anterior superior iliac spine and of the pubic symphysis is determined by percutaneous palpation.

5. The method in accordance with claim 1, wherein the position of the anterior superior iliac spine and of the posterior superior iliac spine is determined by an ultrasonic examination.

6. The method in accordance with claim 2, wherein the position of the anterior superior iliac spine and of the pubic symphysis is determined by an ultrasonic examination.

7. An apparatus for determining an angle of anteversion of an acetabulum in a pelvic bone, comprising:

a navigation system, a navigated position sensor for prominent points of the pelvic bone, and a data processor which is programmed so as to:

calculate from position data of an anterior superior iliac spine at one side of the pelvic bone and from position data of a posterior superior iliac spine at the one side of the pelvic bone, and from position data of a transverse plane of the pelvic bone, an individual plane extending perpendicularly to the transverse plane and passing through the anterior superior iliac spine and said posterior superior iliac spine, rotate this individual plane about an axis of rotation extending perpendicularly to the transverse plane through a predetermined angular magnitude of 38°, and determine an angle between the rotated individual plane and a frontal plane as an angle of anteversion.

8. An apparatus for determining an angle of inclination of an acetabulum in a pelvic bone, comprising:

a navigation system, a navigated position sensor for prominent points of the pelvic bone, and a data processor which is programmed so as to:

calculate from position data of an anterior superior iliac spines at one side of the pelvic bone and from position data of a pubic symphysis), and from position data of a frontal plane of the pelvic bone, an individual plane extending perpendicularly to the frontal plane and passing through said the anterior superior iliac spine and said pubic symphysis, rotate this individual plane about an axis of rotation extending perpendicularly to the frontal plane through a predetermined angular magnitude of 16°, and s determine an angle between the rotated individual plane and a sagittal plane as an angle of inclination.

9. An apparatus in accordance with claim 7, wherein the navigated position sensor is a palpation sensor.

10. An apparatus in accordance with claim 8, wherein the navigated position sensor is a palpation sensor.

11. An apparatus in accordance with claim 7, wherein the navigated position sensor is an ultrasonic sensor.

12. An apparatus in accordance with claim 8, wherein the navigated position sensor is an ultrasonic sensor.

\* \* \* \* \*

UNITED STATES PATENT AND TRADEMARK OFFICE
CERTIFICATE OF CORRECTION

PATENT NO. : 8,394,036 B2
APPLICATION NO. : 12/284619
DATED : March 12, 2013
INVENTOR(S) : Josef Kozak It is certified that error appears in the above-identified patent and that said Letters Patent is hereby corrected as shown below:

In the Claims:

Column 5, in Claim 2, line 16: "non-invasively determining a position of pubic symphysis," should read -- non-invasively determining a position of a pubic symphysis, --

Column 6, in Claim 8, line 26: "data of a pubic symphysis), and from position data of a" should read -- data of a pubic symphysis, and from position data of a --

Column 6, in Claim 8, line 29: "ing through said the anterior superior iliac spine and said" should read -- ing through the anterior superior iliac spine and said --

Column 6, in Claim 8, line 33: "determined angular magnitude of 16°, and s" should read -- determined angular magnitude of 16°, and --

Signed and Sealed this
Fourteenth Day of May, 2013

Teresa Stanek Rea
*Acting Director of the United States Patent and Trademark Office*